United States Patent [19]

Lockridge

[11] Patent Number: 5,720,722
[45] Date of Patent: Feb. 24, 1998

[54] CONNECTOR FOR USE IN SINGLE AND DOUBLE BREAST PUMPING AND BREAST PUMP USING SAME

[75] Inventor: Kathleen A. Lockridge, Crystal Lake, Ill.

[73] Assignee: Medela, Incorporated, McHenry, Ill.

[21] Appl. No.: 585,024

[22] Filed: Jan. 11, 1996

[51] Int. Cl.$^6$ .................................................. A61M 1/06
[52] U.S. Cl. ........................ 604/74; 604/346; 604/283
[58] Field of Search ........................ 604/73–76, 313, 604/315, 346, 119, 320, 905, 32, 246, 248, 283

[56] References Cited

U.S. PATENT DOCUMENTS

| | | | |
|---|---|---|---|
| 4,468,225 | 8/1984 | Tcheraz | 604/248 |
| 4,534,758 | 8/1985 | Akers et al. | 604/85 |
| 4,662,868 | 5/1987 | Cambio, Jr. | 604/32 |
| 4,857,051 | 8/1989 | Larsson | 604/74 |
| 5,007,899 | 4/1991 | Larsson | 604/74 |
| 5,071,403 | 12/1991 | Larsson | 604/74 |

OTHER PUBLICATIONS

Selected pages from "Medela Hospital Catalog," ©1992. Medela, Inc.

*Primary Examiner*—Michael Powell Buiz
*Assistant Examiner*—A. T. Nguyen
*Attorney, Agent, or Firm*—Brinks Hofer Gilson & Lione

[57] ABSTRACT

A connector for use in single and double breast pumping modes of operation of a breast pump has a tubular housing with an internal wall extending across the housing interior and dividing it into two chambers. One chamber has a first nipple extending from the internal wall and into air communication with the second chamber, the first nipple being adapted for attachment of an air tube leading to a breast shield in a single-pumping mode. The other chamber has two nipples extending from the internal wall each of which are in air communication the first chamber. Preferably, the three nipples are joined through a common air/vacuum junction. The second and third nipples are likewise adapted for attachment of an air tube thereto in a double-pumping mode.

8 Claims, 2 Drawing Sheets

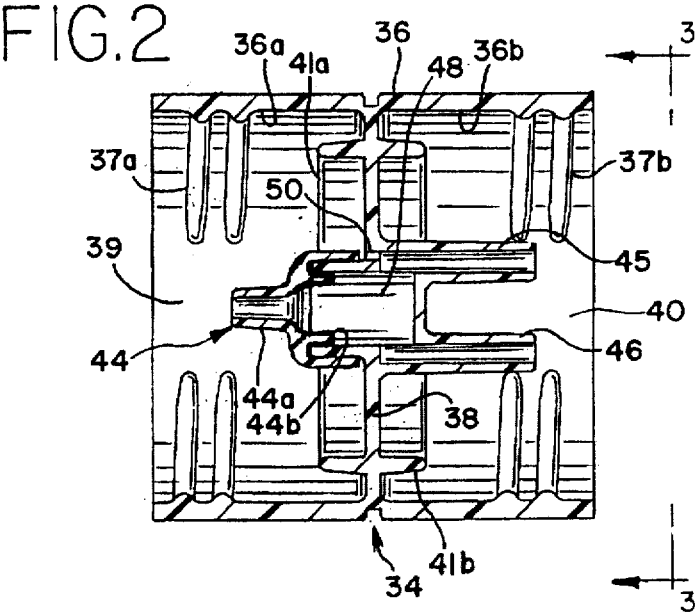
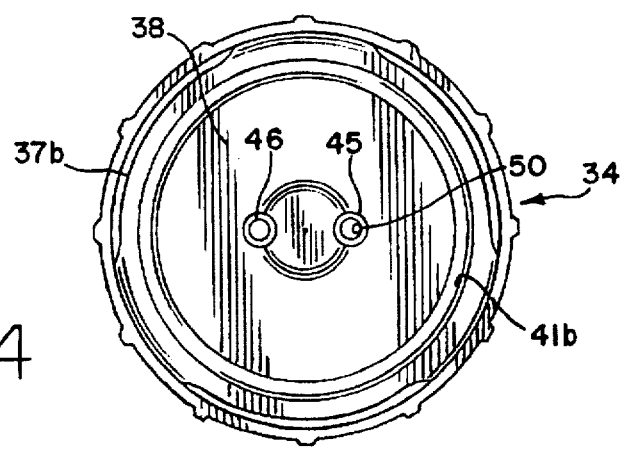
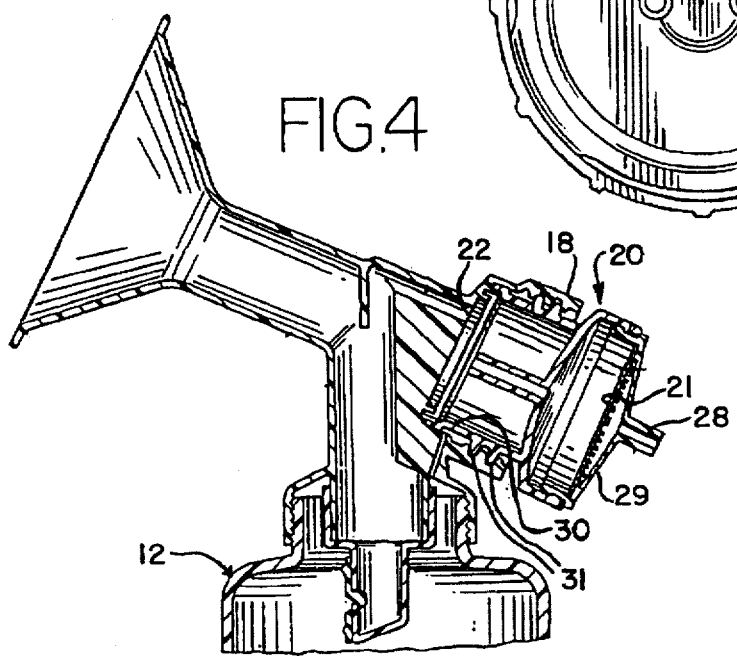

CONNECTOR FOR USE IN SINGLE AND DOUBLE BREAST PUMPING AND BREAST PUMP USING SAME

FIELD OF THE INVENTION

The present invention relates to breastmilk pumps, and more specifically to a breastmilk pump which can be used in both single and double-pumping modes of operation.

BACKGROUND OF THE INVENTION

Breastmilk pumps are well-known, and generally comprise a hood, or shield, that fits over the breast, a vacuum pump connected to the shield for generating an intermittent vacuum (i.e., negative pressure) within the shield, and a receptacle for the expressed milk. The intermittent suction action of the vacuum within the shield serves to pull on and massage the breast and thereby extract milk in an action reminiscent of suckling. The milk so extracted is ordinarily collected in a bottle or other container for storage and later use. Such breast pumps are disclosed in U.S. Pat. Nos. 4,857,051, 5,007,899 and 5,071,403 for example.

It is also well-known to provide a breast pump which can be used in both single (one breast) and double (both breasts) modes of operation. For example, Medela, Inc., to which the present invention is assigned, has in the past provided a "Y" connector for use with its commercialized CLASSIC vacuum pump apparatus. In a double-pumping mode, a single vacuum tube from the vacuum pump is connected to one of the nipples of the "Y", with tubes running to two breast pump assemblies (to carry vacuum to the respective breast shields) connected to the other two nipples of the "Y". Two adapters were further used, each containing a milk barrier to prevent milk from reaching the vacuum pump. An adapter was releasably attached to a respective breast pump assembly through a threaded engagement. A flexible ring, supplied as another piece of the breast pump kit, was further used to cover an air vent in each adapter when used for double-pumping. The air vent was used for negative-pressure equalization when the adapter was used in a single-pumping mode, so that negative pressure in a breast shield used in single-pumping would be approximately the same as when two were used in a double-pumping mode (the latter presenting a greater volume of air to displace). In a single-pumping mode, the "Y" is not required.

This arrangement using the "Y" including two adapters of the foregoing type is disclosed in U.S. Pat. No. 5,071,403, along with the liquid-impervious air-porous membrane across the vacuum line. While a single adapter could be used with the vacuum tube for double-pumping, an extra length of tubing would then be required for connection to the "Y".

SUMMARY OF THE INVENTION

An objective of the present invention was to eliminate a significant number of attachment parts, including the "Y" connector piece previously employed in the double-pumping mode, the flexible ring, and the need for two adapters, to provide a breast pump which used fewer connections and attachments, thereby facilitating easier use of the breast pump and yielding fewer pieces for the user to carry or misplace.

To these and other ends, the present invention provides a connector which can be used in single and double breast pumping modes of operation. The invention comprises a tubular housing having an interior with an internal wall extending across the tubular housing interior, dividing the same into a first and a second chamber.

The first chamber has a port, such as a first nipple therein extending from the internal wall. The first nipple is for attachment of a tube leading to a breast shield of a breast pump assembly, and is further in air communication with the second chamber.

The second chamber has second and third ports, which are preferably nipples extending from the other side of the internal wall. These second and third nipples are likewise for attachment of breast assembly tubes, with each of the second and third nipples being in air communication with the first chamber.

An attachment mechanism is provided for alternately detachably connecting one or the other of the first and second chambers of the tubular housing in a substantially airtight fit in the vacuum line. This attachment is such that in a single-pumping mode the second and third nipples are within the vacuum line; that is, they are not exposed but are enclosed within the vacuum line. The first nipple is thereby only exposed, for attachment of an air tube thereto. In a double-pumping mode, the first nipple is within the vacuum line, with the second and third nipples then exposed for attachment of an air tube to each.

In a preferred embodiment of the invention, the attachment mechanism takes the form of screwthreads formed on the sidewalls of the connector tubular housing which engage with an adapter for attachment of the connector into the vacuum line. The adapter has a rearward base part with a fourth port, such as a nipple extending therefrom which receives the vacuum tube in a snug airtight fit. Vacuum is communicated through the fourth nipple into a tubular forward part of the adapter extending from the rearward base part. The tubular forward part of the adapter is match-threaded to the connector.

In the same preferred form of the invention, the first chamber further includes an air vent through the internal wall and into air communication with the second chamber. The air vent is sized to allow ambient air to be pulled therethrough in the single-pumping mode in sufficient quantity to generate a vacuum level through the first nipple which is about the same as a vacuum level generated through the second and third nipples in the double-pumping mode.

The connector is further preferably designed with the internal passages of the first, second and third nipples all joined together at a common junction defined in the connector. The air vent also extends through the internal wall and into air communication with that junction.

The present invention therefore eliminates the "Y" connector formerly used, while minimizing the number of tubes required for double-pumping. It provides a connector that is readily used in either a single or double-pumping mode through an easy and effective alternative engagement of a handy tubular structure.

The foregoing objectives and advantages of the invention will be further understood upon consideration of the following detailed description of an embodiment of the invention taken in conjunction with the drawings, in which:

BRIEF DESCRIPTION OF THE DRAWINGS

FIG. 2 is an enlarged sectional view of the connector of FIG. 1;

FIG. 3 is an end view taken along line 3—3 of FIG. 2, and

FIG. 4 is a sectional view of the upper portion of a breast pump assembly of the type shown in FIG. 1.

DETAILED DESCRIPTION OF A PREFERRED EMBODIMENT

Figure 1:
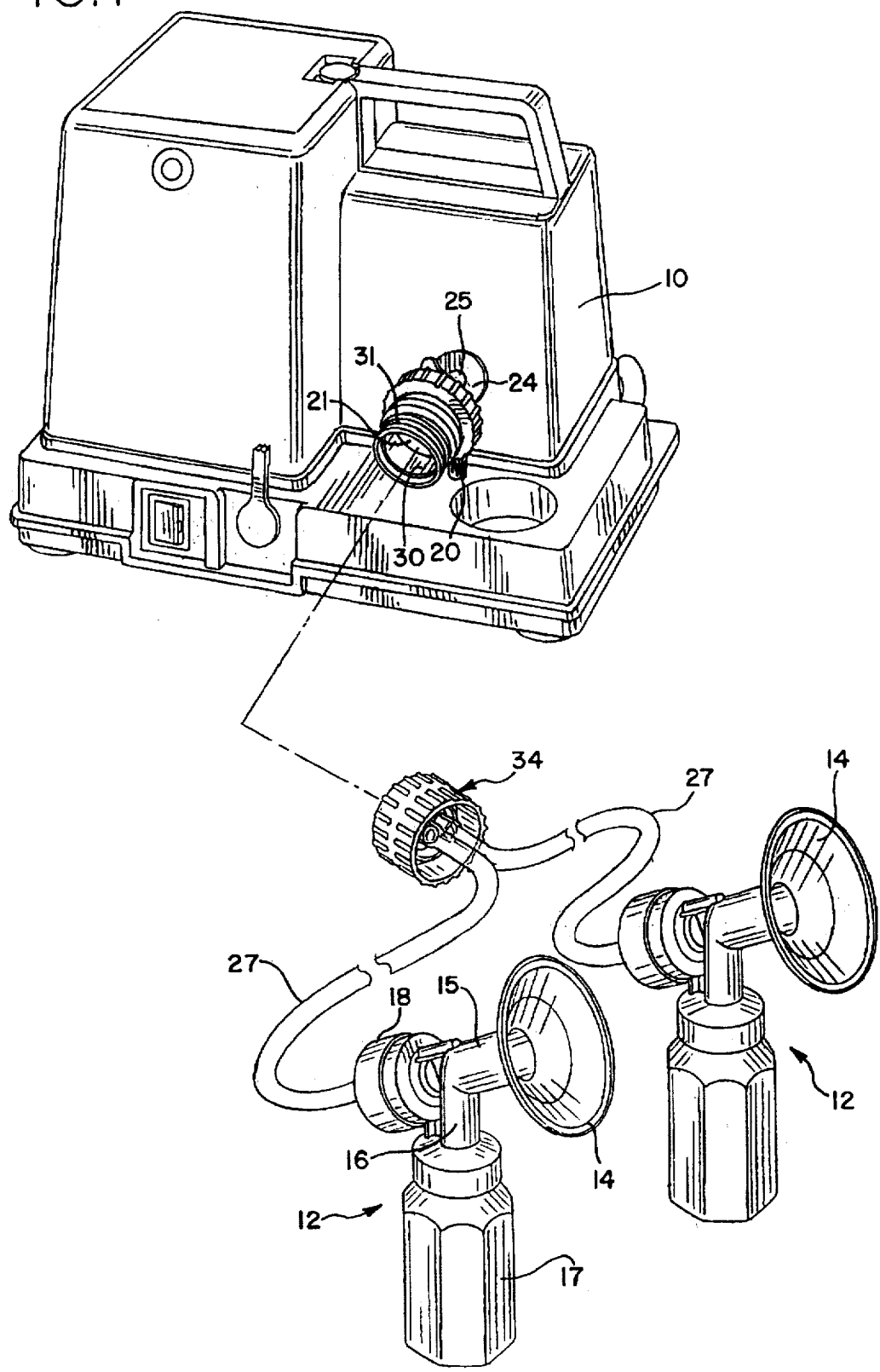
FIG. 1 is a perspective drawing of a breast pump apparatus incorporating a connector of the present invention.

A vacuum pump 10 is used to generate a periodic, or intermittent, vacuum which is then transmitted to one or two breast pump assemblies 12. The vacuum pump illustrated is the CLASSIC pump provided by Medela, Inc., the assignee of the present invention. Any vacuum pump generating a suitable negative pressure could be used, however, such as the LACTINA pump also provided by Medela, and described in U.S. Pat. No. 5,007,899. As referred to herein, vacuum is meant to denote a negative pressure supplied at the breast shield 14 to draw upon a breast placed therein to express milk. Thus, reference to a tube or passage hereafter as an "air" tube or a "vacuum" tube is not necessarily intended to be limiting, since the vacuum levels typically generated are relatively small departures from ambient.

The breast pump assemblies 12 each include, in addition to the shield 14, an extension 15 from the shield 14 which is in fluid communication with a catch or collecting chamber 16. A bottle 17 is attached to the collecting chamber.

A housing 18 is formed on the breast pump assembly 12 which is adapted to receive a manually-driven piston pump (not shown), an adapter 20 which includes a milk-impervious porous barrier 21, or a tube inserted directly into a port 22 in the housing which is in air/vacuum communication with the extension 15 and shield 14. Further details of the breast pump assembly 12 and adapter 20 can be obtained from U.S. Pat. No. 5,071,403, which is incorporated herein by reference.

Vacuum pump 10 has a vacuum outlet 24, with a nipple 25 thereon. Nipple 28 (FIG. 4) of the adapter 20 is received on the outlet nipple 25. That nipple 28, which is generically a port, extends from a rearward base part 29 of the adapter. The adapter 20 also has a tubular forward part 30. The exterior of the tubular forward part 30 has screwthreads 31 formed thereon, which engage with matched-threads on assembly housing 18, for instance, in one alternative mode of use, such as shown in FIG. 4.

A connector 34 is used to switch between single and double modes of breast pumping. Connector 34 has a tubular housing 36 with an internal wall 38. Wall 38 divides the housing 36 into a first chamber 39 and a second chamber 40. The interior sidewalls 36a and 36b of the housing 36 respectively extending from opposite sides of the wall 38 essentially define the foregoing chambers with the wall. The sidewalls 36a, 36b have screwthreads 37a and 37b respectively formed thereon which are matchthreaded to those of the adapter 20. The tubular forward part 30 of the adapter 20 and the interior sidewalls of the connector 34 are sized to screw together in a substantially airtight fit. Ring-like abutments or seal lips 41a, 41b are formed around a respective side of the wall 38 to frictionally engage with the adapter 20 to facilitate this airtight attachment. The adapter 20 is thus alternatively and detachably engaged with either end of the connector 34. Of course, alternative attachment mechanisms could be employed, such as a snap-fit, interference fit, etc.

A first nipple 44 extends from one side of wall 38 into chamber 39. Here, this nipple 44 is formed of a piece 44a which is permanently affixed to a collar 44b surrounding an opening in the wall center.

A second and third nipple 45 and 46, respectively, extend from the other side of wall 38. Each of the nipples 44, 45 and 46 are sized to receive an end of an airtube thereon, and each has an internal passage which join together at a common junction, indicated at 48.

An air vent 50 also extends through the wall 38 adjacent the first nipple 44 and into the nipple 45. The air vent is sized so that when only the first nipple is being used for single breast pumping, in the manner hereafter described, air can leak through the vent hole into the second chamber 40 in a manner to yield a vacuum in a single breast shield which is about the same as when two breast shields are hooked up.

In use, connector 34 is employed in either of two alternative arrangements. In a single breast pumping mode of operation, adapter 20 is screwed into sidewall 36b of tubular housing 36. This encloses second chamber 40, and places the second and third nipples 45 and 46 literally within the vacuum line. One end of a tube 27 is then attached to first nipple 44, with the other end of the tube inserted into the port 22 of the breast pump assembly 12, as through use of a small tubular connector (not shown). A vacuum drawn on second chamber 40 therefore draws through first nipple 44 and additionally through vent 50.

In a double-pumping mode of operation, adapter 20 is screwed into sidewall 36a of tubular housing 36. This serves to enclose first chamber 39, placing first nipple 44 and vent 50 within the vacuum line. Tubes 27 are then attached to exposed nipples 45 and 46 and respective ports 22 of the breast pump assemblies 12.

Thus, while the invention has been described with reference to a particular embodiment, those having skill in the art will recognize modifications of elements and structure which may facilitate the application of the invention, but which still will fall within the scope of the invention.

What is claimed is:

1. A connector assembly for use in switching between single and double breast pumping modes of a vacuum pump having a vacuum line, the connector for use with a first and a second breast pumping assembly, the connector assembly comprising:

a connector having a tubular housing including an interior with an internal wall extending across said tubular housing interior and dividing said housing interior into a first and a second chamber, said first chamber having a first nipple therein extending from said internal wall, said first nipple having an internal passage therethrough and into air communication with said second chamber, said first nipple being adapted for attachment to the first breast pump assembly, said first chamber further including an air vent through said internal wall and into air communication with said second chamber, said second chamber having second and third nipples therein extending from said internal wall, each of said second and third nipples having an internal passage therethrough and into air communication with said first chamber, each said second and third nipples being adapted for attachment to the second breast pump assembly, an adapter for attachment of said connector to the vacuum line, said adapter having a rearward base part with a fourth nipple extending therefrom having an internal passage therethrough, said fourth nipple being adapted for attachment in the vacuum line, said adapter further having a tubular forward part extending from said rearward base part, and an attachment mechanism for connecting said adapter tubular forward part alternately with said first and second chambers of said tubular housing in a substantially airtight fit, whereby said tubular housing can be used in single as well as double breast pumping modes of operation depending upon whether said first or second chamber is attached to said adapter.

2. A breast pumping kit for use in single and double breast pumping of mother's milk, comprising:

two breast pump assemblies each including a breast shield adapted to receive a breast therein for the expression of milk, an extension from said breast shield having a conduit defined therein for carrying milk expressed into said shield, a tube port adapted to be connected to a breast shield tube, said tube port being in air communication with said breast shield through a vacuum passage defined in said extension for generation of a periodic vacuum within said breast shield, and a breast shield tube having one end adapted to connect with said tube port, an adapter having a base and an adaptor port defined through said base, said adaptor port being adapted for attachment to a source of periodic vacuum, a connector having a wall with opposed first and second wall sides, a first connector port being defined on said first wall side and extending into air communication with said second wall side, and second and third connector ports being defined on said second wall side extending into air communication with said first wall side, each said connector port being adapted for attachment to an end of a breast shield tube, said first wall side further including an air vent extending from said first wall side through to said second wall side, an attachment mechanism detachably connecting said adapter with said connector in two alternative attachment configurations, one alternative attachment configuration being a single-pump mode having said second wall side with said second and third connector ports defined therein detachably connected to said adapter base by said attachment mechanism in a substantially airtight fit about said two connector ports, said first connector port defined on said first wall side being connected to a breast shield tube, the other alternative attachment configuration being a double pump mode having said first wall side with said first connector port defined therein detachably connected to said adapter base by said attachment mechanism in a substantially airtight fit about said first connector port on said first wall side and said vent, with said second and third connector ports on said second wall side each being connected to a respective breast shield tube.

3. A connector assembly for use in single and double breast pumping modes of operation of a breast pump including a vacuum pump for generating a periodic vacuum which is communicated through a vacuum line to one or more breast shields, comprising:

a connector having a tubular housing including an interior with an internal wall extending across said tubular housing interior and dividing said housing interior into a first and a second chamber, said first chamber having a first nipple therein extending from said internal wall, said first nipple having an internal passage therethrough and into air communication with said second chamber, said first nipple being adapted for attachment of an air tube thereto, said second chamber having second and third nipples therein extending from said internal wall, each of said second and third nipples having an internal passage therethrough and into air communication with said first chamber, each said second and third nipples being adapted for attachment of an air tube thereto, and attachment means for alternately detachably connecting one of said first and second chambers of said tubular housing in a substantially airtight fit with a vacuum line, such that in a single-pumping mode said second and third nipples are within said vacuum line and said first nipple is only exposed for attachment of an air tube thereto, and in a double-pumping mode said first nipple is within said vacuum line and said second and third nipples are only exposed for attachment of an air tube to each.

4. The connector assembly of claim 3 wherein said first chamber further includes an air vent through said internal wall and into air communication with said second chamber, said air vent being sized to allow ambient air to be pulled therethrough in said single-pumping mode in sufficient quantity to generate a vacuum level through said first nipple which is about the same as a vacuum level generated through said second and third nipples in said double-pumping mode.

5. The connector assembly of claim 4 further comprising an adapter having a rearward base part with a fourth nipple extending therefrom with an internal passage therethrough, said fourth nipple being adapted to attach to a vacuum outlet in the vacuum line in a snug airtight fit, said adapter further having a tubular forward part extending from said rearward base part, said tubular housing having a first sidewall extending from a first wall side of said internal wall and defining said first chamber with said internal wall, and a second sidewall extending from a second wall side of said internal wall opposite to said first wall side and defining said second chamber with said internal wall, said attachment means for alternately detachably connecting one of said first and second chambers of said tubular housing comprising interengaging threads formed on said adapter tubular forward part and on each of said first and second sidewalls of said tubular housing.

6. The connector assembly of claim 5 further including a fluid barrier to the passage of milk carried within said adapter extending across the vacuum line.

7. The connector assembly of claim 4 wherein said internal passages of said first, second and third nipples are joined together at a common junction defined in said internal wall and nipples extending therefrom, and said air vent extends through said internal wall and into air communication with said junction.

8. A breast pumping apparatus having single and double breast pumping modes, comprising:

a vacuum pump which generates a periodic vacuum, said vacuum pump having a vacuum tube and a vacuum outlet, a plurality of tubes for conveying a vacuum generated by said vacuum pump, two breast pump assemblies each including a breast shield adapted to receive a breast therein for the expression of milk, an extension from said breast shield having a conduit defined therein for carrying milk expressed into said shield, said tube port being in air communication with said breast shield through a vacuum passage defined in said extension for generation of a periodic vacuum within said breast shield, a connector having a tubular housing encompassing a housing interior, with an internal wall extending across said tubular housing interior and dividing said housing interior into a first and a second chamber, said tubular housing having a first sidewall extending from a first wall side of said internal wall and defining said first chamber with said internal wall, and a second sidewall extending from a second wall side of said internal wall opposite to said first wall side and defining said second chamber with said internal wall, said first chamber having a first nipple therein extending from said first wall side, said first nipple having an internal passage therethrough and into air communication with said second chamber, said first nipple being adapted for attachment of a first tube thereto, said first chamber further including an air vent through said internal wall and into air communication with said second chamber, said air vent being sized to allow ambient air to be pulled therethrough in a single-pumping mode in sufficient quantity to generate a vacuum level through said first nipple which is about the same as a vacuum level generated in a double-pumping mode, said second chamber having second and third nipples therein extending from said second wall side, each of said second and third nipples having an internal passage therethrough and into air communication with said first chamber, each said second and third nipples being adapted for attachment of a second and a third tube thereto, said internal passages of said first, second and third nipples being joined together at a common junction defined in said internal wall and nipples extending therefrom, said air vent extending through said internal wall and into air communication with said junction, the first, second and third tubes being connected to said first, second and third nipples and extending to a respective tube port of a breast pump assembly, an adapter for attachment of said connector to said vacuum tube, said adapter having a rearward base part with a fourth nipple extending therefrom having an internal passage therethrough, said fourth nipple being adapted to attach to the vacuum outlet in a snug airtight fit, said adapter further having a tubular forward part extending from said rearward base part, and an attachment mechanism for connecting said adapter tubular forward part alternately with said first and second chambers of said tubular housing in a substantially airtight fit comprising interengaging elements formed on said adapter tubular forward part and on each of said first and second sidewalls of said tubular housing, whereby said tubular housing can be used in single as well as double breast-pumping modes of operation depending upon whether said first or second chamber is attached to said adapter.

\* \* \* \* \*